US00PP33201P2

(12) United States Plant Patent
Cain

(10) Patent No.: US PP33,201 P2
(45) Date of Patent: Jun. 29, 2021

(54) GRAPEVINE NAMED 'IFG FORTY-SIX'

(50) Latin Name: ***Vitis interspecific* hybrid**
Varietal Denomination: IFG Forty-six

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 16/974,177

(22) Filed: Nov. 3, 2020

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 206, 207
See application file for complete search history.

(56) References Cited

U.S. PATENT DOCUMENTS

PP20,377 P2 10/2009 Cain

*Primary Examiner* — Susan McCormick Ewoldt

(57) ABSTRACT

This invention is a new and distinct grapevine variety denominated 'IFG Forty-six'. The new grapevine is characterized by producing naturally large size oblong seedless green berries having a very crisp texture, thin skin and which ripen in late season and are tolerant of rain during ripening. Berries are borne on large size clusters which are somewhat tight and require gibberellin to thin.

1 Drawing Sheet

Latin name of the genus and species claimed: *Vitis* interspecific hybrid.

Variety Denomination: 'IFG FORTY-SIX'.

BACKGROUND OF THE INVENTION

The new and distinct Grapevine plant described and claimed herein originated from a hand pollinated cross of the interspecific hybrid 'Arkansas 2756' (not patented) with pollen of 'IFG 104-253'(U.S. Plant Pat. No. 20,377) hybridized in May 2008. The abortive seed traces were subsequently embryo cultured and the resulting 107 seedlings were planted in the field in April 2009. The present variety of grapevine was selected as a single plant in September 2011 and was first asexually propagated by hardwood cuttings in December 2011 near Delano, Kern County, Calif. These resulting cuttings produced second generation plants that were planted during April 2012 near Delano, Kern County, Calif. and were observed for seven years and found to reproduce true-to-type.

BRIEF SUMMARY OF THE INVENTION

The new grapevine 'IFG Forty-six' is characterized by producing naturally large size oblong seedless green berries having a very crisp texture, thin skin and which ripen in late season and are tolerant of rain during ripening. Berries are borne on large size clusters which are somewhat tight and require gibberellin to thin. Berries are responsive to gibberellic acid applications to increase berry size. To the inventor's knowledge, the known variety to which the new grapevine variety is most similar is the 'IFG Forty-two' (U.S. Plant Pat. No. 31,746). 'IFG Forty-six' differs from the 'IFG Forty-two' by having an oblong shape as opposed to the narrow ellipsoid shape of 'IFG Forty-two', by having slightly less crisp flesh texture, and by having a heavier more dense cluster. 'IFG Forty-six' is also somewhat similar to 'Autumn King' (U.S. Plant Pat. No. 16,284) but differs from 'Autumn King' by having much firmer, crisp berry flesh texture, by having a slightly smaller berry size, by having oblong as opposed to ovoid shaped berries and by being able to produce large crops on spur pruned vines as opposed to requiring cane pruning. 'IFG Forty-six' is also somewhat similar to the Thompson seedless variety (not patented) but differs by having much larger, firmer berries, by being able to be spur pruned rather than requiring cane pruning, by being more tolerant of rain during ripening and by ripening approximately eight weeks after 'Thompson Seedless'. 'IFG Forty-six' differs from its maternal parent, the 'Arkansas 2756' by producing larger more oblong berries as opposed to the smaller more oval berries of 'Arkansas 2756', by having a more desirable yellow-green color as opposed to the darker green color of 'Arkansas 2756', and by exhibiting less flesh browning than 'Arkansas 2756'. It differs from its pollen parent, the 'IFG 104-253', by producing slightly larger, more firm berries, by having a more open canopy with weaker lateral shoot growth and by ripening approximately eight weeks later.

BRIEF DESCRIPTION OF THE DRAWING

The accompanying photographic drawing illustrates in full color 'IFG Forty-six'. The photograph was taken outdoors with indirect lighting. The colors are as nearly true as is reasonably possible in a color representation of this type.

The left side of the drawing illustrates a mature leaf.

A mature fruit cluster is represented in the center of the drawing along with a typical berry in cross section.

A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 7-year-old plants of 'IFG Forty-six' grown in the vicinity of Delano, Kern County, Calif. during 2017 to 2019, and is believed to apply to plants of the variety grown under similar conditions of soil and climate elsewhere:

VINE

General:

*Vigor*.—Vigorous.
*Density of foliage*.—Medium to dense.
*Productivity*.—Very productive, producing about 33.2 to 50.0 kg of fruit per vine.
*Root stock*.—Own root.
*Training method*.—Typically spur pruned leaving 2 bud spurs.
*Plant hardiness zone*.—Fully hardy in USDA zone 9A (2012). Not tested in other zones.
*Resistance/susceptibility to typical pests and diseases of Vitis vinifera species*.—Not observed to date.

Trunk:

*Trunk diameter of 7-year-old vines at 30 cm above the soil line*.—Approximately 5.9 cm.
*Shape*.—Medium to somewhat slender.
*Surface texture*.—Medium rough texture.
*Inner bark color*.—The following colors were observed: Greyed-orange: 165A and 174A and 174B.
*Outer bark color*.—Brown: N200A

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Medium.
*Density of erect hairs on tip*.—Absent.
*Color*.—Yellow-green: 144A.

Woody shoot (mature canes):

*Internode length*.—Long: About 12.4 cm.
*Width at node*.—About 1.3 cm.
*Cross section*.—Circular.
*Surface*.—Striate.
*Main color*.—The following colors were observed: Greyed-orange: 165A and 175A and 175B and 175C and 175D and 176A and 176B and 176C.
*Density of erect hairs on nodes*.—None.
*Density of erect hairs on internodes*.—None.
*Axillary shoot vigor at full bloom*.—Weak: Approximately 7.0 cm.

Flowering shoot:

*Vigor during flowering*.—Medium.
*Attitude during flowering on shoots not tied*.—Semi-erect.
*Color*.—Dorsal side of internodes — Yellow-green: 144A.
*Color*.—Ventral side of internodes — Yellow-green: 144A.
*Color*.—Dorsal side of nodes — Yellow-green: 144A.
*Color*.—Ventral side of nodes — Yellow-green: 144A.
*Density of prostrate hairs on nodes*.—Very sparse.
*Density of erect hairs on nodes*.—None.
*Density of prostrate hairs on internode*.—None to very sparse.
*Density of erect hairs on internode*.—None.
*Anthocyanin coloration of buds*.—Absent.

Tendrils:

*Distribution on the shoot (at full flowering)*.—Discontinuous.
*Length of tendril*.—Very long: About 34.9 cm.
*Thickness of tendril 2 cm from base*.—About 2.6 mm.
*Color*.—Yellow-green: 144C.
*Form*.—Mixture of bifurcated and trifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 144B.
*Average intensity of anthocyanin coloration of six distal leaves prior to flowering*.—Absent.
*Density of prostrate hairs between veins (lower surface)*.—Very sparse.
*Density of prostrate hairs on veins (lower surface)*.—Very sparse.
*Density of erect hairs between veins (lower surface)*.—Absent.
*Density of erect hairs on veins (lower surface)*.—Absent to very sparse.

Mature leaves (opposite first cluster):

*Average length*.—About 13.0 cm.
*Average width*.—About 16.5 cm.
*Mature leaf size*.—Medium to large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Undulate.
*Blistering surface of blade upper surface*.—Weak.
*Leaf blade tip*.—In the plane of the leaf.
*Leaf apex*.—Broadly acute.
*Leaf margin*.—Serrate.
*Undulation of margin*.—Slight.
*Undulation of blade between main and lateral veins*.—Slight undulation over entire area.
*Shape of teeth*.—Mostly both sides convex with a few teeth being both sides straight.
*Length of teeth*.—Short: Approximately 4.0 mm.
*Width of teeth*.—Medium: Approximately 8.6 mm.
*Ratio length/width of teeth*.—Medium: Approximately 0.5.
*Shape of upper lateral sinuses*.—Closed.
*Depth of upper lateral sinuses*.—Shallow.
*General shape petiole sinus*.—Half open.
*Shape of base of upper leaf sinuses*.—V-shaped.
*Tooth at petiole sinus*.—Absent.
*Density of prostrate hairs between veins on lower surface of blade*.—Sparse.

*Density of erect hairs between veins on lower surface of blade*.—Absent to very sparse.
*Density of prostrate hairs on main veins on lower surface of blade*.—Sparse.
*Density of erect hairs on main veins on lower surface of blade*.—Sparse.
*Density of prostrate hairs on main veins on upper surface of blade*.—Very sparse.
*Density of erect hairs on main veins on upper surface of blade*.—None.
*Autumn coloration of leaves*.—Leaves can be a single color or combination of colors, in a mottled pattern or on the edges of the leaves. The following colors were observe: Greyed-yellow: 162A and 162B and 162C.

Upper surface:
*Color*.—Green: 137A.
*Anthocyanin coloration of main veins* (*lower surface*).—Absent.
*Color of main veins*.—Yellow-green: 144C.
*Surface appearance*.—Semi-glossy.
*Blistering surface of blade*.—Weak.

Lower surface:
*Color*.—Yellow-green: 146B.
*Anthocyanin coloration of main veins* (*lower surface*).—Absent.
*Color of main veins*.—Yellow-green: 144D.
*Glossiness*.—Weak.
*Surface texture*.—Smooth.
*Surface appearance*.—Dull.

Petiole:
*Length*.—About: 11.8 cm.
*Diameter of petiole 2 cm from blade*.—About 3.0 mm.
*Petiole color*.—Yellow-green: 144A.
*Length of petiole compared to middle vein*.—Slightly longer.
*Density of prostrate hairs on petiole*.—None or very sparse.
*Density of erect hairs on petiole*.—None.

Buds:
*Bud fruitfulness*.—Basal: mostly fruitful.
*Position of first fruitful shoot on previous season cane*.—$1^{st}$ to $2^{nd}$ node.
*Dormant bud length*.—About 5.9 mm.
*Dormant bud width in the proximal/distal plane*.—About 3.6 mm.
*Dormant bud color*.—The following colors were observed: Greyed-orange: 165A and 175A.
*Time of bud burst*.—Approximately Mar. 17, 2019.

FLOWERS

General:
*Flower sex*.—Hermaphrodite.
*Length of single flower, unopened*.—About 3.9 mm.
*Width of single flower*.—Unopened: About 1.7 mm. Opened: About 7.4 mm.
*Stamen length*.—About 4.2 mm.
*Stamen count*.—5.
*Pollen color*.—Yellow: 10A.
*Pistil length*.—About 3.5 mm.
*Pistil color*.—Yellow-green: 144A.
*Length of first inflorescence*.—Medium to long: About 18.6 cm long and 13.6 cm wide.
*Position of first flowering and fruiting node*.—$3^{rd}$ and $4^{th}$ nodes (current season growth).
*Number of inflorescence per flowering shoot*.—1.1 to 2: About 1.5.
*Time of bloom*.—Early to mid-season as compared with similar varieties in the growing area of Delano, Calif.
*Date of full bloom*.—About May 8, 2019.

FRUIT

General:
*Ripening period*.—Late season: Approximately Sep. 3, 2019.
*Use*.—Fresh market.
*Keeping quality*.—Excellent, remains commercially acceptable when stored up to 8 weeks at 0° C. and high Relative humidity.
*Refractometer test*.—Soluble solids: About 23.2 Brix.
*Brix/acid*.—About 61.0.
*Titratable acidity*.—About 0.38.
*Juice ph*.—About 3.87.
*Juice color*.—Yellow-green: 145C.

Cluster:
*Mature cluster length* (*peduncle excluded*).—About 22.6 cm.
*Mature cluster width*.—About 16.6 cm.
*Mature cluster weight*.—About 1108 g.
*Bunch density*.—Medium: densely distributed berries, pedicels not visible, berries movable.
*Number of berries*.—About 153.
*Form*.—Conical.

Peduncle:
*Lignification of peduncle*.—Weak.
*Diameter of peduncle*.—About 5.1 mm.
*Length of peduncle*.—Medium: Approximately 3.5 cm.
*Color of peduncle*.—Yellow-green: N144A.

Berry:
*Uniformity of size*.—Uniform.
*Single berry weight*.—About 8.9 g natural; to about 9.1 g when treated with gibberellic acid.
*Shape*.—Oblong.
*Seeds*.—Absent.
*Cross section*.—Circular.
*Berry dimensions*.—Longitudinal axis: About 3.3 cm: Horizontal axis: About 2.1 cm.
*Pedicel length*.—About 6.1 mm.
*Pedicel width*.—About 1.8 mm.
*Pedicel color*.—Yellow-green: 145C.
*Berry firmness*.—Very Firm.
*Particular flavor*.—Neutral.
*Bloom* (*cuticular wax*).—Strong.
*Berry separation from pedicel*.—Medium to somewhat easy.
*Skin color* (*without bloom*).—Yellow-green: N144A.
*Flesh color*.—Yellow-green: 145D.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine plant as herein illustrated and described.

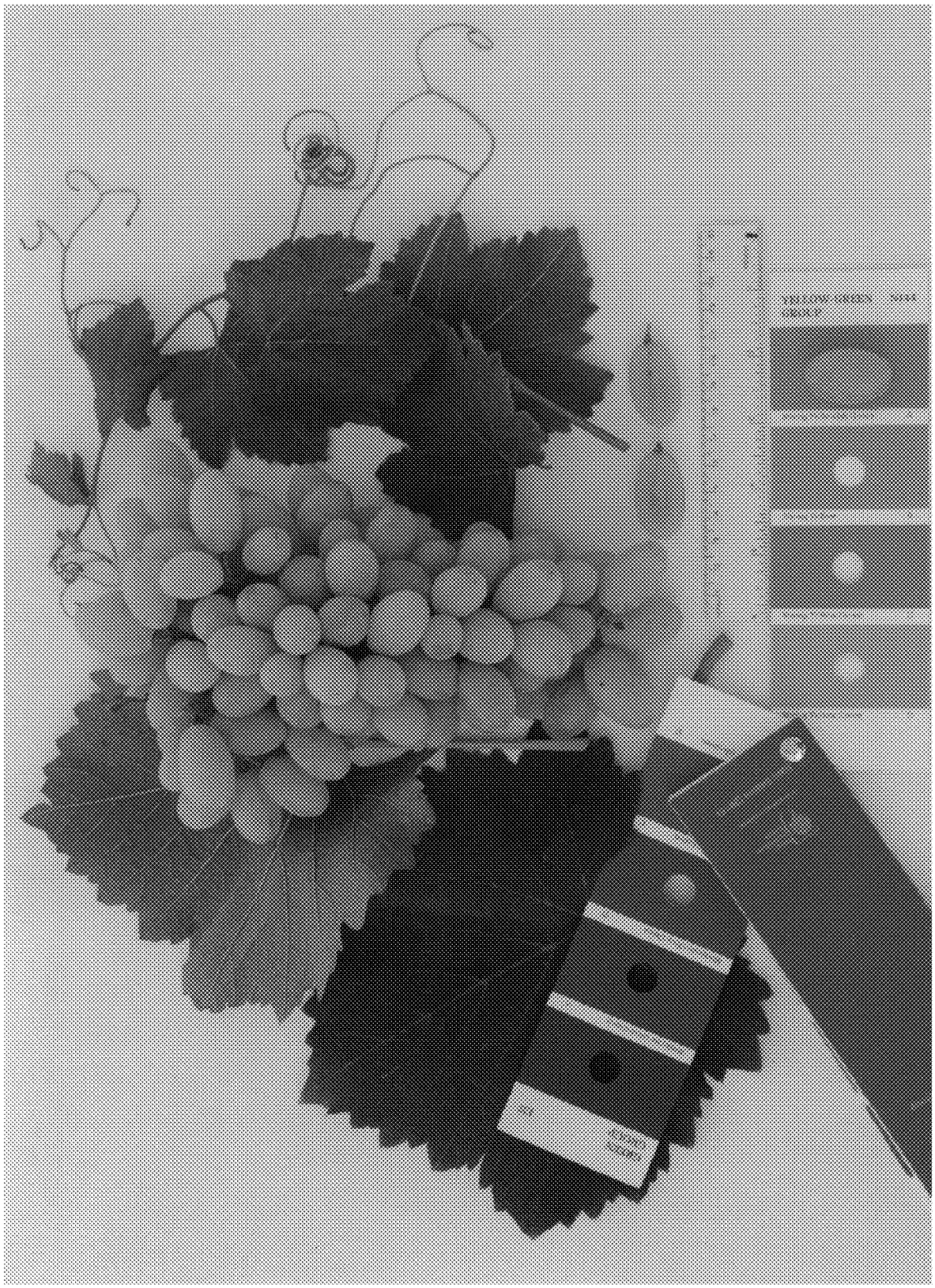

* * * * *